United States Patent [19]

Kropkowski et al.

[11] Patent Number: 5,046,493
[45] Date of Patent: Sep. 10, 1991

[54] NASAL DISPENSER

[76] Inventors: James Kropkowski, 166 E. Passaic, Rutherford, N.J. 07070; Jesse L. Colodner, 22 Walter St., Pearl River, N.Y. 10965

[21] Appl. No.: 156,473

[22] Filed: Feb. 16, 1988

[51] Int. Cl.⁵ ............................................ A61M 15/00
[52] U.S. Cl. ......................... 128/203.15; 128/203.18; 604/58
[58] Field of Search ...................... 128/203.15, 203.18; 604/57, 58, 54, 73, 173, 181, 183, 186, 218, 246, 59, 60, 211; 222/325, 335, 490, 209, 630, 631

[56] References Cited

U.S. PATENT DOCUMENTS

| 658,436 | 9/1900 | Groth | 128/203.18 |
| 2,587,215 | 2/1952 | Priestely | 128/203.18 |
| 3,203,455 | 8/1965 | Horabin | 604/183 |
| 4,151,933 | 5/1979 | Myers | 272/325 |
| 4,240,418 | 12/1980 | Rosskamp et al. | 128/203.18 |
| 4,570,630 | 2/1986 | Elliott et al. | 128/203.18 |

FOREIGN PATENT DOCUMENTS

| 448214 | 9/1926 | Fed. Rep. of Germany | 604/57 |
| 0628931 | 9/1978 | U.S.S.R. | 128/203.18 |
| 2041763 | 9/1980 | United Kingdom | 128/203.18 |
| 2165159 | 4/1986 | United Kingdom | 128/203.18 |

Primary Examiner—Randall L. Green
Assistant Examiner—K. M. Reichle
Attorney, Agent, or Firm—Iman Abdallah

[57] ABSTRACT

This dispenser is designed to be employed in delivering a prescribed quantity of medication into a nostril of a patient. Primarily, it consists of a main body having a U-shaped chamber therein, for containing a measured quantity of medication received from a barrel of the device by rotation of a plunger in the barrel, and the main body is transparent for visually observing a pair of painted and indented dots provided in the leg portions of the medication chamber. An oral blow tube is also provided for air pressure to be applied to the chamber to dispense the medication out of the chamber into a flexible and transparent nasal tube that is insertable into a nostril of a patient.

6 Claims, 1 Drawing Sheet

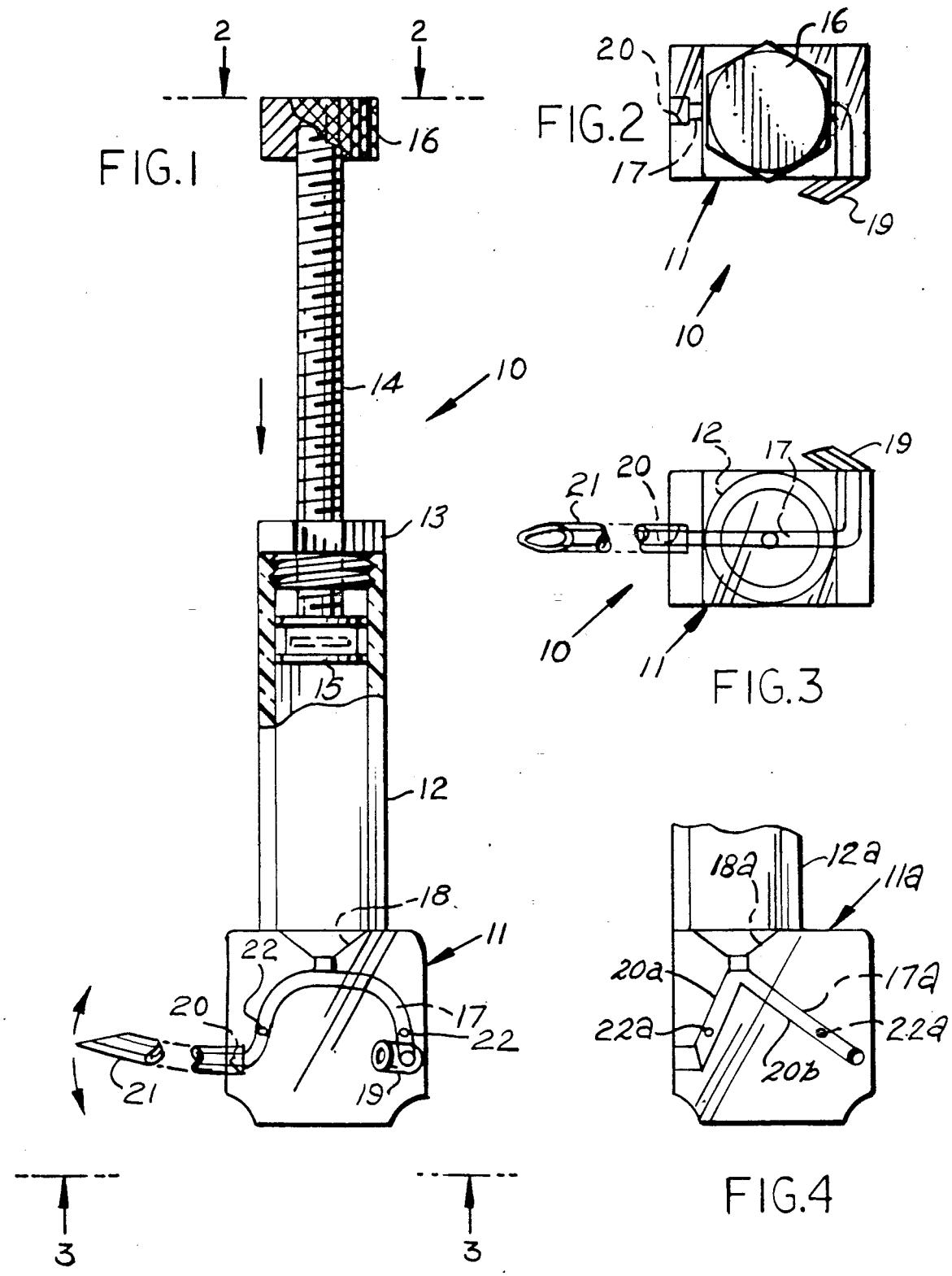

NASAL DISPENSER

BACKGROUND AND FIELD OF THE INVENTION

This invention relates to medication dispensers, and more particularly, to a nasal dispenser.

DESCRIPTION OF PRIOR ART

Nasal dispensers have been devised in the prior art, but while such units may be suitable for the particular purpose to which they address, they would not be as suitable for the purpose of the present invention as hereinafter will be described.

The principal object of this invention is to provide a nasal dispenser that will be of such design, as to be employed to measure minute quantities of medication accurately and easily.

Another object of this invention is to provide a nasal dispenser that will dispense medication via nasal inhalation, the patient employing his or her own oral blowing power exerted through an oral blow tube that will be attached to the apparatus at its main body, and the medication will be discharged out of the dispenser through another side of the main body, via a flexible nasal tube inserted into the patient's nostril.

Another object of this invention is to provide a nasal dispenser that will be easily washed in warm soapy water or sterilized, and the user need not worry about his or her living accommodations, traveling, leaky ice, etc. The present invention also eliminates the need to carry medication vials, measuring paraphenalia, etc.

Another object of this invention is to provide a nasal dispenser that will be sanitary, as the patient uses the same hermetically drawn medication for several applications, thereby reducing the probability of sepsis from constant exposure of the the medication to air. The design is also such, that its dot calibrated medication chamber measures a tiny dose by means of a simple turn of a threaded plunger.

A further object of this invention is to provide a nasal dispenser that will eliminate the need of a separate measuring tube, a filling syringe, a separate medication bottle, and cumbersome refrigeration methods. A further object of this invention is to provide a nasal dispenser that will be of such design, as to include a cold pack that will be employed to keep the dispenser stationary and cool for a period of twelve hours.

SUMMARY OF THE INVENTION

A nasal dispenser comprises a clear body of rectangular configuration having an attached oral blow tube at one end of a medication chamber, and a separate flexible nasal tube is inserted into the cannula opening at the other side of the body. A hollow cylinder is also integrally attached and has the capacity of containing an approximate seven day supply of medication.

Further provided, is a threaded plunger for forcing medication into the calibrated medicine chamber of the body.

BRIEF DESCRIPTION OF FIGURES

FIG. 1 is a greatly enlarged vertical view of the instant invention, shown in elevation and partly broken away;

FIG. 2 is a view taken along the line 2—2 of FIG. 1;

FIG. 3 is a view taken along the line 3—3 of FIG. 1, and

FIG. 4 is a fragmentary vertical view of a modified form of the invention, shown in elevation.

DETAILED DESCRIPTION

Accordingly, a dispenser 10 is shown to include a transparent main body 11 having a similarly transparent barrel 12 integrally attached thereto. Barrel 12 provides for receiving a medication and is also provided with a screw cap 13 threaded into its upper open end, and an externally threaded plunger 14 is threaded into cap 13 and includes a rubber piston 15 fixedly secured to its lower end. A knurled head 16 is provided on the other end of plunger 14 for ease of rotation thereof. A "U"-shaped medication chamber 17 is defined within main body 11 and intersects with a centrally disposed and frusto-conical sump 18 formed within main body, and a transparent oral blow tube 19 is fixedly secured over one end of medicine chamber 17 of the exterior of main body 11. A recessed portion 20 aligning with the opposite end of chamber 17, frictionally receives one end of a transparent and flexible nasal tube 21, and calibrated measurement of medication to a 0.1 ml quantity, is indicated by the two painted and indented dots 22 on chamber 17.

It shall be noted, that all of the elements herein described are fabricated of clear plastic material, with the exception of the piston, and the preferrable length of dispenser 10 is three inches long. Also, the oral blow tube 19 is preferrably one half of an inch long and the separate and flexible nasal tube 21 is approximately three inches long.

In use, the plunger 14 is rotated in a clock-wise direction, causing medication to be forced into chamber 17 of the main body 11. Counterclock-wise rotation of the plunger 14, vacuums the medication back into the storage barrel 14 from the calibrated chamber 17, so as to enable the measurement to be adjusted precisely, and plunger 14 may be rotated back and forth until the measurement is accurate. The chamber 17 extends to ends of the main body 11, for accommodating slightly more medicine than 0.1 ml which enables adjustment without loss of medication.

When medication is calculated and ready for dispensing, one end of the flexible nasal tube 21 is inserted into 20 of the main body 11, chamber 17 in which chambers the medication that is held constant by a vacuum effect, and the other end of the nasal tube 21 is inserted gingerly into one nostril of the patient.

The patient places the oral blow tube in his/her mouth, and as the patient blows into the oral blow tube 19, the measured medication is forced through the flexible nasal tube and dissipated into the nostril.

To fill, insert one end of the flexible nasal tube 21 into the end of the main body 11 that dispenses medication, and place the other end of the flexible nasal tube into a 2.5 ml. size medication bottle. With the plunger 14 fully inserted into the barrel 12 of dispenser 10, medication is drawn into the barrel 12 by rotating the plunger 14 counter clock-wise, thereby hermetically drawing the medication into the barrel 12.

Referring now to FIG. 4 of the drawing, a modified main body 11a includes a barrel 12a, a sump portion 18a, a chamber 17a, and painted dots 22a.

In FIG. 4, a modified main body 11a, barrel 12a and sump portion 18a are shown to be constructed in a substantially similar manner as the main body 11, barrel 12 and frusto-conical sump 18 shown in FIG. 1. Barrel 12a, however, is disposed in off-set relation to main body 11a. Chamber 17a is a substantially inverted V-shaped member being attached in operable connection at its vertex with sump portion 18a. One leg 20a of V-shaped chamber 17a extends to the exterior wall of main body 11a for receipt of a flexible nasal tube 21 (FIG. 1) and the second leg 20b of chamber 17a extends to the exterior wall of main body 11a for receipt of an oral blow tube 19 (FIG. 1). Two painted and indented dots 22a are respectively disposed on legs 20a and 20b of chamber 17a. A dispenser having a lower portion formed as shown in FIG. 4 is operated in the same manner as heretofore described for the dispenser 10 shown in FIGS. 1, 2 and 3.

While various changes may be made in the detailed construction, such details will be within the spirit and scope of the present invention, as defined by the appended claims:

We claim:

1. A nasal dispenser for self-dispensation of medication to the nostril of the user, comprising:

a hollow cylindrical barrel having a first open end for receipt of medication therein and a second open end;

means for regulating the flow of medication from said barrel, said regulating means comprising a piston plunger including a plunger having a knurled head attached at one end of said plunger and a rubber piston attached at the opposite end of said plunger, said piston plunger being moveably and coaxially disposed in said barrel with said piston being within said barrel and said plunger and said knurled head extending out of said first open end of said barrel to permit the piston plunger to be moved longitudinally within said barrel;

a main body integral with said barrel and disposed at the second open end of said barrel, said main body having an elongated chamber and means for passing medication from said barrel to said chamber formed therein, said passing means comprising a frusto-conical sump fluidly connected at its apex with said chamber and at its base with the second open end of said barrel, said chamber extending to the exterior wall of said main body at two distinct points;

means for enabling air to be blown through said chamber by the user for dispensation of medication held therewithin, said enabling means comprising an oral blow tube fixedly attached to said chamber at said first distinct point; and means for passing said medication from said chamber to the nostril of the user, said passing means comprising a nasal tube fixedly attached to said chamber at said second distinct point.

2. A nasal dispenser as described in claim 1 wherein the first end of said barrel includes interior threads, said barrel further including an exteriorly threaded cap including a central opening having threads formed therein and said plunger being exteriorly threaded and engaging the threaded opening to permit longitudinal movement of said plunger by rotation thereof.

3. A nasal dispenser as described in claim 2 wherein said barrel and said main body are formed of transparent material and said chamber includes indicia means for visual indication of the dosage of medication contained within said chamber.

4. A nasal dispenser as described in claim 3 wherein said indicia means comprises a pair of painted, indented dots disposed in spaced relationship from each other.

5. A nasal dispenser as described in claim 1 wherein said chamber is formed by a substantially inverted-U-shaped tubular passage.

6. A nasal dispenser as described in claim 1 wherein said chamber is formed by a substantially inverted-V-shaped tubular passage.

* * * * *